United States Patent
Pedersen-Bjergaard et al.

(10) Patent No.: US 8,317,991 B2
(45) Date of Patent: Nov. 27, 2012

(54) PROCESS FOR ELECTROKINETIC MIGRATION THROUGH LIQUID MEMBRANES

(76) Inventors: Stig Pedersen-Bjergaard, Oslo (NO); Knut Einar Rasmussen, Eiksmarka (NO)

(*) Notice: Subject to any disclaimer, the term of this patent is extended or adjusted under 35 U.S.C. 154(b) by 1262 days.

(21) Appl. No.: 11/993,464

(22) PCT Filed: Jun. 30, 2006

(86) PCT No.: PCT/NO2006/000251
§ 371 (c)(1), (2), (4) Date: Jan. 21, 2008

(87) PCT Pub. No.: WO2007/004892
PCT Pub. Date: Jan. 11, 2007

(65) Prior Publication Data
US 2010/0072066 A1    Mar. 25, 2010

(30) Foreign Application Priority Data
Jun. 30, 2005 (NO) .................................. 20053226

(51) Int. Cl.
*G01N 27/447* (2006.01)
*G01N 27/453* (2006.01)
(52) U.S. Cl. ........ 204/540; 204/541; 204/543; 204/548; 204/601; 204/644
(58) Field of Classification Search ............... 204/450, 204/451, 540, 541, 543, 601, 548, 644; 205/688, 205/703
See application file for complete search history.

(56) References Cited

U.S. PATENT DOCUMENTS

| | | | | |
|---|---|---|---|---|
| 3,963,567 A * | 6/1976 | Cole | | 204/535 |
| 3,992,435 A * | 11/1976 | Donohue et al. | | 205/418 |
| 5,637,202 A * | 6/1997 | Harrington et al. | | 204/469 |
| 5,650,055 A | 7/1997 | Margolis | | |
| 5,938,909 A * | 8/1999 | Guo et al. | | 204/619 |
| 6,627,061 B2 | 9/2003 | Mani | | |
| 6,830,670 B1 * | 12/2004 | Viovy et al. | | 204/605 |
| 2002/0060154 A1 * | 5/2002 | Vigh | | 204/548 |
| 2003/0006142 A1 * | 1/2003 | Nair et al. | | 204/631 |
| 2003/0019763 A1 | 1/2003 | Conlan | | |
| 2004/0000482 A1 | 1/2004 | Wang | | |
| 2004/0118688 A1 * | 6/2004 | Dumas | | 204/548 |

FOREIGN PATENT DOCUMENTS
WO    0033050    6/2000

OTHER PUBLICATIONS

T. Ho, S. Pedersen-Bjergaard, K. Rasmussen. "Liquid-phase microextraction of protein-bound drugs under non-equilibrium conditions." The Analyst. Apr. 2002. vol. 127, Issue 5. pp. 608-613.*

(Continued)

*Primary Examiner* — Keith Hendricks
*Assistant Examiner* — Steven A. Friday
(74) *Attorney, Agent, or Firm* — Christian D. Abel

(57) ABSTRACT

Device and Process for isolating, purifying, concentrating and/or enriching at least one organic compound by electrokinetic migration through liquid membranes by use of an electronic potential and chambers with a preset pH value is described in the present application. The liquid membranes contain an organic solvent capable of transporting an ionized form of said at least one organic compound.

54 Claims, 8 Drawing Sheets

OTHER PUBLICATIONS

E. Gunther, D. Stone, R. Gerwien, P. Bento, M. Heyes. "Prediction of clinical drug efficacy by classification of drug-induced genomic expression profiles in vitro." Proceedings of the National Academy of Sciences of the United States of America. Aug. 2003. vol. 100, Issue 16. pp. 9608-9613.*

R. Langer. "New methods of drug delivery." Science. Sep. 1990. vol. 249, Issue 4976. pp. 1527-1533.*

Ho, T.S. et al, "Liquid-phase microextraction of PC hydrophilic drugs by carrier-mediated transport" Journal of Chromatography A, Elsevier, Amsterdam, NL, vol. 998, No. 1-2, May 23, 2003, pp. 61-72, XP004428503 ISSN: 0021-9673.

Serga V et al: "Extraction of Nickel by Liquid PC membranes in an Electric Field" Separation Science and Technology, vol. 35, No. 2, 2000, pp. 299-313, XP001247160.

* cited by examiner

PROCESS FOR ELECTROKINETIC MIGRATION THROUGH LIQUID MEMBRANES

FIELD OF THE INVENTION

The present invention relates to new processes for isolation, purification, concentration and/or enrichment of an organic or biochemical compound through elektrokinetic migration, as well as a device for use in said process.

BACKGROUND OF THE INVENTION

The analytical organic chemistry and biochemistry is faced with the problem of providing a compound to be detected in a solution that is suitable for detection by one or more of the commonly known methods. One problem may be that the compound appears in a complex mixture from which it must be isolated. Another problem may be that the compound may be present in a very low concentration. A further problem may be that the sample including the compound to be detected, is very small.

There has therefore been developed many different methods for separating, isolating, concentrating and purifying organic compounds. These are well-known procedures for a person skilled in the art and examples are 2-phase extraction (e.g. aqueous phase-organic phase), and 3 phase extractions (e.g. aqueous phase-organic phase-aqueous phase).

From WO0033050 there are known methods and apparatus for 2-phase liquid and 3-phase liquid microextraction for obtaining a high enrichment of an analyte in the acceptor solution. However, the process of microextraction is based on diffusion of the analyte and this is a slow process. Further, the achievable end concentration of the analyte depends on the equilibrium conditions for each of two 2-phase-systems, and may result in very low yields if any.

Even though the above-mentioned processes have been automated, they are still time consuming and generate a lot of waste organic solvent.

In order to improve the required time for this type of isolation procedures, a further development has constituted of the introduction of elektrokinetic migration.

It is well known that ionized chemical and biochemical substances migrate in solution under the application of an electrical potential difference. This type of transport, which is called electrokinetic migration, is the basis for electrophoresis, and is also widely used for isolation purposes both in industrial applications (purification) and in the field of analytical chemistry (sample preparation).

Frequently, isolation based on electrokinetic migration is carried out in an aqueous one-phase system. One important example of this is electrodialysis, where ionized chemical substances are transferred from an aqueous donor compartment, through the pores of a ion-exchange membrane filled with the same aqueous medium, and into an aqueous acceptor compartment. In electrodialysis, migration selectivity, which is responsible for isolation, is gained by the presence of small pores in the polymeric membrane, preventing larger molecules from entering the acceptor compartment. Electrodialysis is an important industrial purification and desalting process, and has also been reported as a sample preparation technique in analytical chemistry.[1-4] However, the ion-exchange membranes used in electrodialysis processes are easily polluted and must be replaced frequently.

Electrokinetic migration has also been accomplished,[23,24] in a 5-compartment dialyzer with two platinum electrodes and a rigid anion-exchange membrane, where it was shown that nickel ions could cross two two-phase boundaries. The work reported has focused on fundamental migration theory of nickel ions in a system with relatively thick membranes of organic solvent ($\approx$0.2 cm).

There is a need for new, improved processes and devices for isolation, purification, enrichment and/or concentration of an organic compound from a solution, wherein the organic compound is present in a complex mixture or in low concentrations. Further there is a need for new processes giving a high yield of the required organic compound. There is further a need for new processes, which makes it possible to achieve a high purity, and last but not least there is a need for new processes by which the isolation or purification step proceeds significantly faster. Also, there is a need for new processes wherein the environmental issue of large amount of waste organic solvents is resolved.

SUMMARY OF THE INVENTION

These problems are solved by the present invention through processes and devices according to this invention as defined in the attached claims.

Thus, according to the present invention there is provided a device, comprising
  a first hydrophilic donor solution, having a pre-set pH, comprising at least one ionized or partially ionized organic compound
  and a second hydrophilic acceptor solution having a pre-set pH;
  a liquid membrane comprising an immobilized organic solvent, which membrane is placed in fluid contact with both said donor solution and said acceptor solution so that it separates said donor solution and said acceptor solution, and through which organic solvent a current and said at least one ionized organic compound can traverse;
  a first electrode to be placed in contact with the donor solution;
  a second electrode to be placed in contact with the acceptor solution;
  and a voltage source for applying a voltage over said electrodes.

The invention further provides for a process for elektrokinetic migration of an organic compound in a 3-phase system, comprising the steps of
  providing a first hydrophilic donor solution comprising at least one organic compound to be transferred from said donor solution to an acceptor solution;
  optionally adjusting the pH of said donor solution to a level where said organic compound is either positively or negatively ionized;
  providing a second hydrophilic acceptor solution;
  optionally adjusting the pH of said acceptor solution to a level wherein said compound, to be transferred from the donor solution to the acceptor solution, is ionized;
  providing a liquid membrane comprising an immobilized organic solvent, which is substantially immiscible with water, through which a current and said at least one ionized organic compound can traverse;
  and placing said membrane in fluid contact with said donor solution and said acceptor solution, so that it separates said donor solution and said acceptor solution;
  providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution.

The invention further provides for a process for concentration and/or enrichment of at least one organic compound, comprising the steps of
- providing a first hydrophilic donor solution comprising at least one organic compound to be transferred from said donor solution to an acceptor solution;
- optionally adjusting the pH of said donor solution to a level where said organic compound is either positively or negatively ionized;
- providing a second hydrophilic acceptor solution;
- optionally adjusting the pH of said acceptor solution to a level wherein said compound, to be transferred from the donor solution to the acceptor solution, is ionized;
- providing a liquid membrane comprising an immobilized organic solvent, which is substantially immiscible with water, through which a current and said at least one ionized organic compound can traverse;
- and placing said membrane in fluid contact with said donor solution and said acceptor solution, so that it separates said donor solution and said acceptor solution;
- providing a first electrode to be placed in fluid contact with the donor solution and a second electrode to be placed in fluid contact with the acceptor solution;
- applying a voltage over said electrodes to promote the migration of said organic compound from the donor solution through the liquid membrane to the acceptor solution.

The invention further provides for a process for preparing a sample for analysis, comprising the steps of
- providing a first hydrophilic donor solution comprising at least one organic compound to be transferred from said donor solution to an acceptor solution;
- optionally adjusting the pH of said donor solution to a level where said organic compound is either positively or negatively ionized;
- providing a second hydrophilic acceptor solution;
- optionally adjusting the pH of said acceptor solution to a level wherein said compound, to be transferred from the donor solution to the acceptor solution, is ionized;
- providing a liquid membrane comprising an immobilized organic solvent, which is substantially immiscible with water, through which a current and said at least one ionized organic compound can traverse;
- and placing said membrane in fluid contact with said donor solution and said acceptor solution, so that it separates said donor solution and said acceptor solution;
- providing a first electrode to be placed in fluid contact with the donor solution and a second electrode to be placed in fluid contact with the acceptor solution;
- applying a voltage over said electrodes to promote the migration of said organic compound from the donor solution through the liquid membrane to the acceptor solution;
- optionally adjusting the pH of the acceptor solution to transfer said organic compound from an ionised to a non-ionized state and/or transferring the organic compound into an organic solvent,
- and detecting said organic compound by a suitable detector system and/or checking for biological activity in a biological test system.

The invention further provides for a process for purification of a sample, comprising the steps of
- providing a first hydrophilic donor solution comprising at least one organic compound to be transferred from said donor solution to an acceptor solution;
- optionally adjusting the pH of said donor solution to a level where said organic compound is either positively or negatively ionized;
- providing a second hydrophilic acceptor solution;
- optionally adjusting the pH of said acceptor solution to a level wherein said compound, to be transferred from the donor solution to the acceptor solution, is ionized;
- providing a liquid membrane comprising an immobilized organic solvent, which is substantially immiscible with water, through which a current and said at least one ionized organic compound can traverse;
- and placing said membrane in fluid contact with said donor solution and said acceptor solution, so that it separates said donor solution and said acceptor solution;
- providing a first electrode to be placed in fluid contact with the donor solution and a second electrode to be placed in fluid contact with the acceptor solution;
- applying a voltage over said electrodes to promote the migration of said organic compound from the donor solution through the liquid membrane to the acceptor solution;
- optionally isolating said at least one organic compound through removal or replacement of the solvent, optionally after adjusting the pH of the solution.

Definitions

The processes and device of the present invention are useful for the isolation, purification, concentration and/or enrichment of an organic compound in a sample. In the context of this application the terms isolate/isolating/isolation are used generally when describing and defining features in said processes and device, which also applies to processes or devices for purifying, concentrating or enriching an organic compound according to this invention.

The term "organic compound" in the present context has the usual meaning in the art. Especially, in the context of this application, the term "organic compound" is meant to specify an organic compound having an acid or basic entity. Through such an entity the compound can be transferred into its ionic counterpart through pH-adjustment of the donor solution.

Organic compounds are further in the present context intended to encompass both non-biological and biological compounds. Examples of non-biological organic compounds are organic pharmaceuticals, drugs, colouring agents, poisons, pollutants, food additives and metabolites of these. Examples of a biological compound according to this invention are DNA, proteins, peptides, amino acids, carbohydrates, lipids, polysaccharides fatty acids and phospholipids.

The term "donor solution" is intended to specify a solution comprising at least one organic compound in a hydrophilic solvent, wherein said organic compound is in a dissolved state in said solvent.

Further, the donor solution may be a sample taken directly from a source, wherein the organic compound is already in a dissolved state in a hydrophilic solvent. This may for instance be a biological sample from one of the biological fluids of a person, a water sample from drinking water or wastewater, a sample from a preparative or industrial biochemical, organic or fermentation process. Examples of biological samples are blood, serum, urine, salvia, sputum, semen, cell lysate, cell fluid, breast milk or spinal fluid.

The donor solution may alternatively be a solution prepared from a dissolved sample by further dilution with a suitable hydrophilic solvent.

Further, a donor solution may also be prepared from a non-dissolved sample, such as a solid or a semi-solid sample through dissolution of said sample or parts of said sample in a suitable solvent or solvent mixture, from which a donor solution according to this invention may be prepared directly or by one or more intermediate steps.

The term "hydrophilic solvent" as used in the context of this application has the usual meaning in the art. Especially, this term is meant to specify water or a hydrophilic organic solvent or a mixture of a hydrophilic solvent and water.

The hydrophilic solvent is most preferred water. However, the hydrophilic solvent may be water in admixture with a hydrophilic organic solvent, wherein the organic solvent may be present in the range from 0-100% by weight; more preferred in the range from 0-50% by weight and still more preferred from 0-20% by weight. Examples of additions to an aqueous donor solution of organic hydrophilic solvent may be 1, 2, 3, 4, 5, 6, 7, 8, 9 or 10% by weight.

The hydrophilic organic solvent can be any such hydrophilic solvent which dissolves the at least one organic compound. Further, the hydrophilic organic solvent is preferably miscible with water. However it may be immiscible with water if a single hydrophilic phase is created at the chosen concentration of said water-immiscible organic solvent in a substantially aqueous donor solution. Examples of preferred hydrophilic organic solvents are methanol, ethanol, acetonitrile and DMSO.

The term "acceptor solution" as used in the context of the present application, is a hydrophilic solution, which is suitable for accepting an ionised organic compound after said ionised organic compound has passed through the liquid membrane.

Both the donor and acceptor solutions must have a pH at which the organic compound is partially or fully ionised. This can be achieved by addition of a suitable acid or base, as is well known in the art. Thus, such a suitable acid is any acid that can adjust the pH of the donor solution to a level within the range of pH 1-6, whereby an organic compound carrying a basic group is ionised to a cation. Correspondingly, such a suitable base is any base that can adjust the pH of the donor solution to a level within the range of pH 8-14, whereby an organic compound carrying an acidic group is ionised to an anion. Examples of suitable acids are HCl, HBr, HCOOH, $CH_3COOH$, $H_2SO_4$ and $H_3PO_4$. Examples of suitable bases are NaOH, $Na_2CO_3$, $NaHCO_3$ and $NH_3$.

The term "liquid membrane" is intended to have the usual meaning in the art. Especially, the term liquid membrane is intended to specify a thin immobilized organic phase. The thinness of the membrane is essential to achieve a successful migration of an ionised organic molecule across said membrane.

The actual size of such a liquid membrane will be dependent on several factors such as the organic compound to be isolated, the liquid membrane's organic solvent, the conductivity of said organic solvent, and the applied voltage.

It is preferred that the thickness of the liquid membrane is in the range of 0.01-1000 µm, depending on the intended use.

Thus, for lab-scale sample preparation, the membrane thickness is normally in the range of 1-500 µm.

For use of the present invention in micro-chip analysing systems, the membrane thickness will normally be in the range of 1-300, especially 5-50 µm.

For isolation of organic compounds from a single cell, the membrane thickness will be presumably be in the range of 0.01-10 µm, or 0.05-1.0 µm.

For large scale isolations, purifications and concentrations or enrichments, such as in industrial or preparative scale organic, biochemical or fermentation processes, the thickness of the liquid membranes is considered likely to be in the upper end of the range, such as from 100-1000 µm. However, large scale processes according to the invention may also conducted with a number of small devices according to this invention bundled together, and in such a case each of the membranes will be in the range mentioned above for lab-scale sample preparations.

The organic phase may be immobilized in any suitable structure, which structure does not interfere with said elektrokinetic migration, and in which the organic solvent may be stably immobilized for the duration of the elektrokinetic migration process. The structure must further allow an electrical current as well as said at least one ionised, organic compound to traverse the organic solvent immobilized in said structure.

The immobilization is most preferred achieved by use of a micro-porous hollow fibre, into the pores of which an organic solvent is immobilized by immersing the hollow fibre into said solvent. A wide range of different hollow fibres is commercially available today. A hollow fibre to be used in the present invention must be selected in consideration of the organic solvent to be included in the liquid membrane, so that the chosen hollow fibre can immobilize the organic solvent during the time span necessary for the elektrokinetic migration process in question.

Suitable hollow fibres for this invention are both polar and non-polar hollow fibres. Examples of non-polar hollow fibres are hollow fibres of polypropylene, Teflon™ and polyethylene.

Examples of porous materials suitable for immobilisation of an organic solvent include polyolefines, sulfone polymers, such as polysulphone, polyethersulphone, or polyacrylate, fluorinated polymers, such as polyvinylidene fluoride (PVDF), acrylic polymers, polyamides or nylons, polyesters, polyurethanes, polycarbonates, polystyrenes, polyvinyl chlorides, polyacrylonitriles, or copolymers thereof or mixtures thereof.

In a particularly preferred embodiment, the polymer is a polyolefin, such as polyethylene, polypropylene, polytetrafluoroethylene (PTFE), poly(tetrafluoroethylene-coethylene), or polyethylene-polyvinyl chloride copolymer.

It is further referred to for instance WO 02/088672 and WO 00/33050 for details on hollow fibres, and these references are incorporated herein in their entirety.

Another immobilization structure for the liquid membrane is a polymeric film that is swellable in an organic solvent. Such a film may have any suitable shape such as for instance a sheet or a tube. Examples of such swellable polymeric films are polyethylene or polyacrylate films. The immobilization of organic solvent is achieved by immersing said polymeric film in the organic solvent and letting it swell.

The term "organic solvent" in the liquid membrane as used in the context of the present application is intended to have the usual meaning for a person skilled in the art. Especially the term organic solvent is meant to signify any organic solvent having a conductivity that allows an electrical current as well as an ionised organic compound to traverse it. In some cases this can be achieved by adding at least one conductivity-improving additive to the organic solvent.

Thus, said organic solvent should be a solvent with a certain polarity or water content in order to achieve sufficient conductivity and to ensure penetration of the electrical field.

In one embodiment, said organic solvent is different from the solvent of the donor and/or acceptor solution. More preferably, said organic solvent is immiscible with the solvent of the donor and/or acceptor solution, more preferably immiscible with water.

Examples of suitable organic solvents for isolation of alkaline substances are nitrobenzene, 1-isopropyl nitrobenzene, 2-nitrophenyl octyl ether, nitropentane, nitropropane, 1-ethyl-2-nitrobenzene and 2-nitrophenyl pentylether. Examples of solvents for isolation of acidic substances are octanol, heptanol, nonanol and decanol. An example of an especially suitable organic solvent is 2-nitrophenyl octyl ether (NPOE).

The electrical current that traverses the liquid membrane may in principle be any electrical current that does not give rise to a turbulent electrolysis process. It is considered preferably that it should be in the lower microampere range, i.e. preferable less than 100 μA, but normally more than 0.01 μA.

The term "conductivity-improving additive" as used in the present context is intended to signify an agent that will improve the solubility of the ionised organic compound in the liquid membrane.

Compounds having the right properties for a conductivity-improving additive will be apparent to a person skilled in the art. Examples of such conductivity-improving additives are tertiary amines and phosphates, such as N-trioctylamine and di(2-ethyl hexyl)-phosphates.

The conductivity-improving agent may be added to the organic solvent of the liquid membrane in any suitable range for achieving an improved solubility and migration of said organic compound. Normally, said conductivity-improving agent will be added in a amount in the range from 0-50% by volume of the organic solvent, such as in the range from 5-20% or from 10-30% by volume.

The electrodes that are suitable for use in the present invention may be any commercially available electrode.

The voltage applied to said electrodes is normally in the range of 0.01V-30,000V; more preferred 0.1V-10,000V, even more preferred 1V-1000V, still more preferred 1-500V; and especially preferred 1V-300V. The applied voltage is most preferred a DC voltage. In some cases the applied voltage is a pulsed voltage A means for agitating at least one of the solutions may be added to the device, such as to the donor solution or acceptor solution, or both. Such means may be any suitable means as known to a skilled person in the art. Such means may for instance be stirring means or shaking means.

Embodiments

One embodiment of the present invention is a process for sample-preparation in the usual analytical scale. In such an embodiment the sample size is normally in the range of 10 μL-1000 mL.

Another embodiment is a process for isolation of an organic compound in connection with preparative organic synthesis or biochemical synthesis. A further embodiment is a process for purification of an organic compound in connection with preparative organic synthesis or biochemical synthesis. Another embodiment is a process for concentration and/or enrichment of an organic compound in connection with preparative organic synthesis or biochemical synthesis. In such embodiments the sample size will normally be in the range of 1 mL-10 L.

One embodiment of the present invention is a process for industrial concentration and/or enrichment of an organic compound, wherein the sample size normally is very large, for instance from 100 L upwards. In one embodiment for industrial concentration or enrichment, the donor solution is fed continuously. In another embodiment for industrial concentration or enrichment, the donor solution is fed intermittently, for instance in dependence of the concentration of the organic compound in the acceptor solution reaching a certain level. In a further embodiment both the acceptor solution and the donor solution are fed continuously or intermittently after a pre-set time or when a certain concentration of the organic compound in the acceptor solution has been reached.

A further embodiment of the present invention is a process for industrial purification of an organic compound, wherein the sample size normally is very large, for instance from 100 L upwards. In one embodiment for industrial purification, the donor solution is fed continuously. In another embodiment for industrial purification the donor solution is fed intermittently, for instance in dependence of the concentration of the organic compound in the acceptor solution reaching a certain level. In a further embodiment both the acceptor solution and the donor solution are fed continuously or intermittently after a pre-set time or when a certain concentration of the organic compound in the acceptor solution has been reached.

A further embodiment is a process for purification of a sample by removal of the desired organic compound to the acceptor solution. Another embodiment is a process for purification of at least one organic compound by removal of at least one unwanted organic compound by transferring it to the acceptor solution.

Still another embodiment is a process for industrial isolation of at least one wanted organic compound, wherein the sample size normally is very large, for instance from 100 L upwards. In one embodiment for industrial isolation, the donor solution is fed continuously. In another embodiment for industrial isolation the donor solution is fed intermittantly, for instance in dependence of the concentration of the organic compound in the acceptor solution reaching a certain level. In a further embodiment both the acceptor solution and the donor solution are fed continuously or intermittently after a pre-set time or when a certain concentration of the organic compound in the acceptor solution has been reached.

Still another embodiment of the invention is a process which further comprises a step wherein the acceptor solution is used for quantitative and/or qualitative detection of the organic compound, optionally after adjusting the pH of the solution to a level where said at least one organic compound is transferred to a non-ionized state and/or transferring said organic compound to an organic solvent(s). Such detection may further include a detection of the biological activity of said at least on organic compound in a biological test system.

Other embodiments of the invention are devices for use in the processes of the present invention. Thus, one such embodiment is a device for analytical lab-scale sample preparation; a second embodiment is a device for purification of a sample from a preparative organic process; a third such embodiment is a device for purification of a sample from a biochemical process.

Still another embodiment is a device for concentration and/or enrichment of at least one organic compound. A further embodiment is a device for industrial scale concentration and/or enrichment of at least one organic compound.

A further embodiment is a device for isolation of at least one organic compound from a single cell.

A further embodiment is a device for micro-chip analyses, wherein a device according to the present invention is combined with a micro-chip analyser.

The invention provides a device comprising in a first feature a donor solution that is a substantially aqueous solution.

In another feature of this invention the donor solution is an aqueous solution having an addition of a water-miscible organic solvent in the range of 0.1-50% by weight, especially 1-20%; or 2-10 or 0.1-0.5%.

In still another feature, the donor solution is a substantially non-aqueous solution comprising a hydrophilic organic solvent.

In another feature said non-aqueous solvent of the donor solution has an addition of an aqueous solution or water in the range of 0.1-50% by weight, especially 1-20%; or 2-10 or 0.1-0.5%.

In still another feature, the donor solution is a mixture of an aqueous solution and a non-aqueous hydrophilic solution. In such features the ratio aqueous solution:hydrophilic organic solution of the mixture is in the range from 2:1 to 1:2, especially 1:1.

In a further feature of the invention, the acceptor solution is a substantially aqueous solution. In another feature of the invention the acceptor solution has an addition of a water-miscible organic solvent in the range of 0.1-50% by weight, especially 1-20%; or 2-10 or 0.1-0.5%.

In still another feature, the acceptor solution is a substantially non-aqueous solution comprising a hydrophilic organic solvent.

In a further feature, the acceptor solution has an addition of an aqueous solution or water in the range of 0.1-50% by weight, especially 1-20%; or 2-10 or 0.1-0.5%.

In still another feature of the invention, the acceptor solution is mixture of an aqueous solution and a non-aqueous hydrophilic solution.

In such features the ratio aqueous solution:hydrophilic organic solution of the mixture is in the range from 2:1 to 1:2, especially 1:1.

The invention further provides for a device, wherein the donor solution is comprised in a first compartment and the acceptor solution is comprised in a second compartment and the two compartments have relative volumes in the range donor compartment:acceptor compartment of 10,000:1 to 1:100, or 1000:1 to 1:10, more preferred 100:1 to 1:1. Such a device having a much larger donor compartment compared to the acceptor compartment is especially suitable for concentrating and/or enriching at least one organic compound in a sample, wherein said at least one organic compound appears in a very low concentration in the donor solution.

The invention further provides for a device wherein the donor solution is comprised in a first compartment and the acceptor solution is comprised is a second compartment and the two compartments have relative volumes of 1:2 to 2:1, or 1:1. Such a device is especially suitable for isolating or purifying at least one organic compound, in cases wherein the achievable concentration of the at least one organic compound in the acceptor solution is satisfactory. It is considered that this may be the case when the organic compound is an intermediate is a preparative organic or biochemical procedure. In such cases the acceptor solution may be subjected to one or more further reaction steps to prepare a desired end product.

The invention further provides for a device, wherein the first and second solutions are placed in compartment(s) where at least one of said compartments are movable in relation to the other compartment and/or to the liquid membrane. It is most preferred that the compartment of the first solution, i.e. the donor solution is movable in relation to the liquid membrane.

It is especially preferred that a device according to this invention has a disposable liquid membrane.

In the following, the invention will be elucidated by the discussion of experiments performed by the inventors. This experimental section will further give detailed explanation of some of the figures mentioned above.

EXPERIMENTAL SECTION

Electrokinetic Cross-Membrane Isolation (ECMI)

Figure 1:
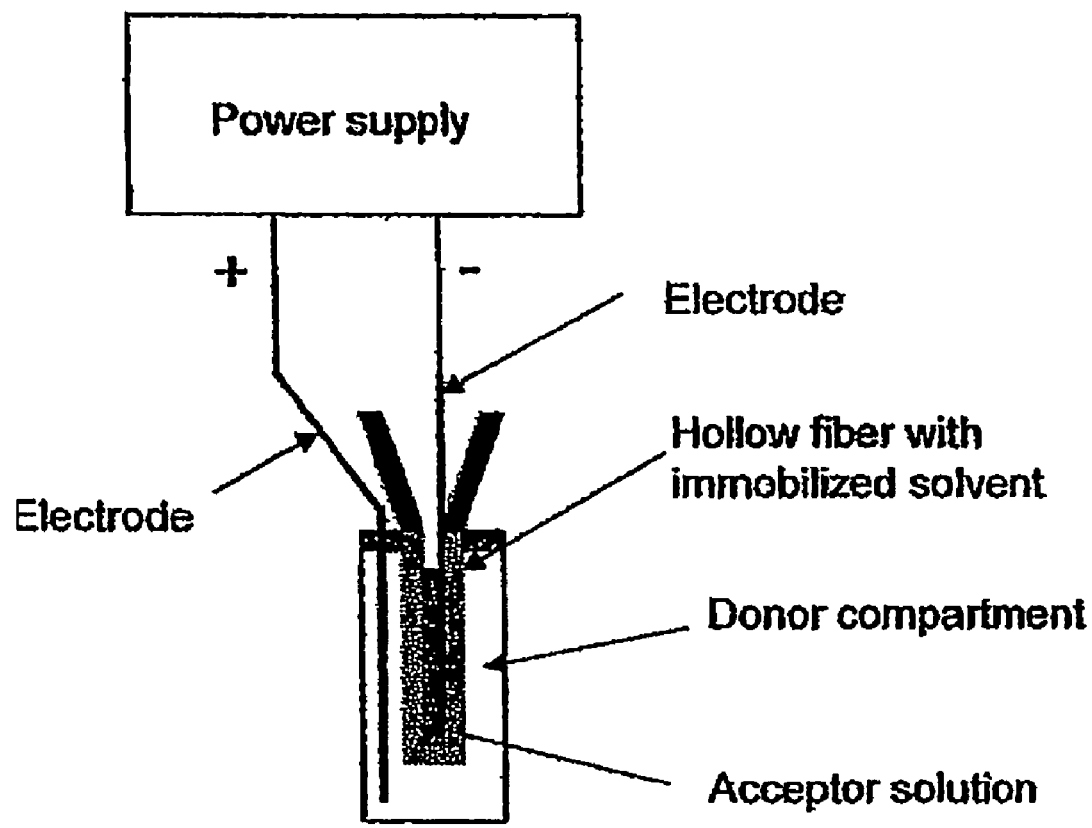
FIG. 1. Schematic illustration of one embodiment for electrokinetic cross-membrane isolation (ECMI), having a tubular shaped membrane.
Figure 2:
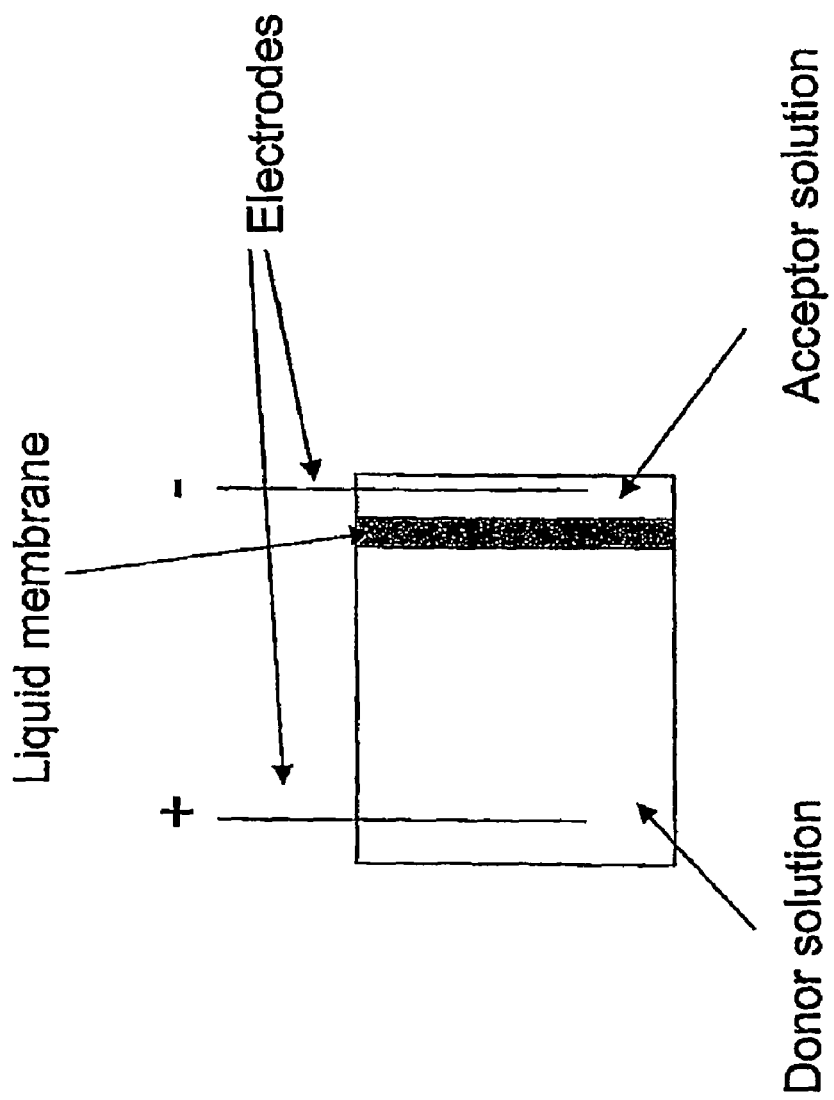
FIG. 2. Schematic illustration of another embodiment of a device of the invention having a flat membrane.

The equipment used for electrokinetic cross-membrane isolation (ECMI) is illustrated in FIG. 1. The DC power supply used was a model XFR 300-9 (Xantrex, Burnaby, BC, Canada) with a programmable voltage in the range 0 to 300 V, providing currents in the range 0 to 9 A. Simple steel wires with a diameter of 0.2 mm were used as electrodes in the sample and acceptor solutions, and were connected to the power supply. As sample compartment, 800 µL polypropylene vials with cap were used with a height of 35 mm and with an internal diameter of 5.2 mm (unknown supplier). In some experiments a 1 ml polypropylene vial with an internal diameter of 7 mm were utilized. The porous hollow fiber used for immobilization of the artificial liquid membrane and for housing the acceptor solution was a PP Q3/2 polypropylene hollow fiber (Membrana, Wuppertal, Germany) with an internal diameter of 1.2 mm, with a 200 µm wall thickness, and with 0.2 µm pores. The ECMI was agitated at 1200 rpm during the experiments with a Vibramax 100 agitator (Heidolph, Kelheim, Germany).

ECMI was performed according to the following procedure; 300 µl acidified sample solution was filled into a polypropylene vial, and the positive electrode was placed in the sample. A 3.1 cm piece of polypropylene hollow fiber was closed in the lower end by mechanical pressure, whereas the upper end was connected to a 2.2 cm length pipette tip of polypropylene as a guiding tube. The hollow fiber and the guiding tube were then inserted through the cap of the sample vial. The hollow fiber was dipped for 5 s in the organic solvent serving as the artificial liquid membrane (typically 2-nitrophenyl octyl ether, nitrobenzene, 1-isopropyl nitrobenzene, octanol or heptanol), and excess of solvent was removed with a medical wipe. With a micro syringe, 30 µL of acceptor solution was filled into the hollow fiber, and the negative electrode was placed in the acceptor solution. Finally, the hollow fiber with acceptor solution was placed into the sample, and voltage (typically 300 V) was applied for 5 minutes. After electrokinetic cross-membrane isolation, the acceptor solution was collected with a micro syringe, and was transferred to a micro insert for the capillary electrophoresis instrument.

Capillary Electrophoresis.

Capillary electrophoresis was performed with a MDQ instrument (Beckman, Fullerton, Calif., USA) equipped with a UV-detector. Separations were accomplished in a 75-μm-i.d. fused-silica capillary with an effective length of 20 cm (Beckman). The running buffer was 15 mM phosphate adjusted to pH 2.7 with ortho-phosphoric acid. The instrument was operated at 20 kV, which generated a current level of approximately 50 μA. Samples were introduced by hydrodynamic injection at 0.5 psi for 5 s. Detection was accomplished at 200 nm utilizing a 100×800 μm slit.

Chemicals.

Pethidine hydrochloride, nortriptyline hydrochloride, methadone hydrochloride, haloperidol, loperamide hydrochloride, amphetamine sulphate, methamphetamine sulphate, hydralazine hydrochloride, metaraminol hydrochloride, cimetidine, sotadol, practolol and atenolol were all obtained from Sigma-Aldrich (St. Louis, Mo., USA). 2-nitrophenyl octyl ether, dihexyl ether, 2-octanone, silicone oil AS 4, and di(2-ethylhexyl)phosphate were from Fluka (Buchs, Switzerland). 1-octanol and dodecyl acetate were purchased from Sigma, kerosene was from Norsk Medisinaldepot (Oslo, Norway), soy-bean oil and peppermint oil were from a local pharmacy. Hydrochloric acid, disodium hydrogen phosphate dodecahydrate, and sodium dihydrogen phosphate monohydrate were from Merck (Darmstadt, Germany), and formic acid was from Fluka. Human plasma was obtained from Ulleval hospital (Oslo, Norway)

Standard Solutions and Biological Samples.

A stock solution containing 1 mg/mL of each of pethidine, nortriptylin, methadone, haloperidol, and loperamide was prepared in ethanol and stored at −20° C. protected from light. Sample solutions (in pure water) were prepared by dilution of this stock solution by 10 mM HCl. This stock solution was also utilized to spike human plasma and urine samples.

Calculation of Recovery and Enrichment.

Recovery (R) during the cross-membrane isolation was calculated according to the following equation for each analyte:

$$R = n_{a,final}/n_{s,initial} \times 100\% = (V_d/V_s)(C_{a,final}/C_{s,initial}) \cdot 100\% \quad (1)$$

where $n_{s,initial}$ and $n_{a,final}$ are the number of moles of analyte originally present in the sample and the number of moles of analyte finally collected in the acceptor solution, respectively. $V_a$ is the volume of acceptor phase, $V_s$ is the volume of sample, $C_{a,final}$ is the final concentration of analyte in the acceptor phase, and $C_{s,initial}$ is the initial analyte concentration within the sample.

Enrichment (E) during the cross-membrane isolation was calculated according to the following equation for each analyte:

$$E = C_{a,final}/C_{s,initial} \quad (2)$$

Results and Discussion

Initial Experiments.

The basic experiments were performed in a device for electrokinetic cross-membrane isolation (ECMI) as illustrated in FIG. 1. The sample solution (300 μL), which was acidified with HCl (pH≈2) prior to ECMI to ionize basic analytes of interest or made alkaline with NaOH to ionize acidic analytes of interest, was filled into a small polypropylene tube, and a positive electrode was placed in this solution and connected to the power supply. A porous hollow fiber of polypropylene, which was sealed in the lower end, was dipped in 2-nitrophenyl octyl ether for 5 seconds to immobilize the solvent in the pores in the wall of the hollow fiber. This thin layer of organic solvent served as the artificial liquid membrane, the volume was approximately 15 μL, and the thickness was approximately 200 μm corresponding to the wall thickness of the hollow fiber. Inside the lumen of the hollow fiber, 30 μL of a 10 mM hydrochloric acid solution in water was injected which served as the acceptor solution, and a negative electrode connected to the power supply was placed in this acceptor solution. Finally, the hollow fiber was placed in the sample, and 300 V was applied over the electrodes for 5 minutes. The acceptor solution was collected after this by a micro syringe and transferred for analysis by capillary electrophoresis. Twenty different basic drugs were selected as model analytes, namely: Practolol, metaraminol, sotalol, atenolol, cimetidine, hydralazine, nortriptyline, amfetamine, metamfetamine, methadone, hydroxyzine, pethidine, mepyramine, promethazine, haloperidol, fluphenazine, phencyclidine, clomipramine, loperamide and clemastine. The model analytes had various degrees of hydrophobicity as shown by their log P values (1-octanol/water partition coefficients) in Table 5.

Figure 3:
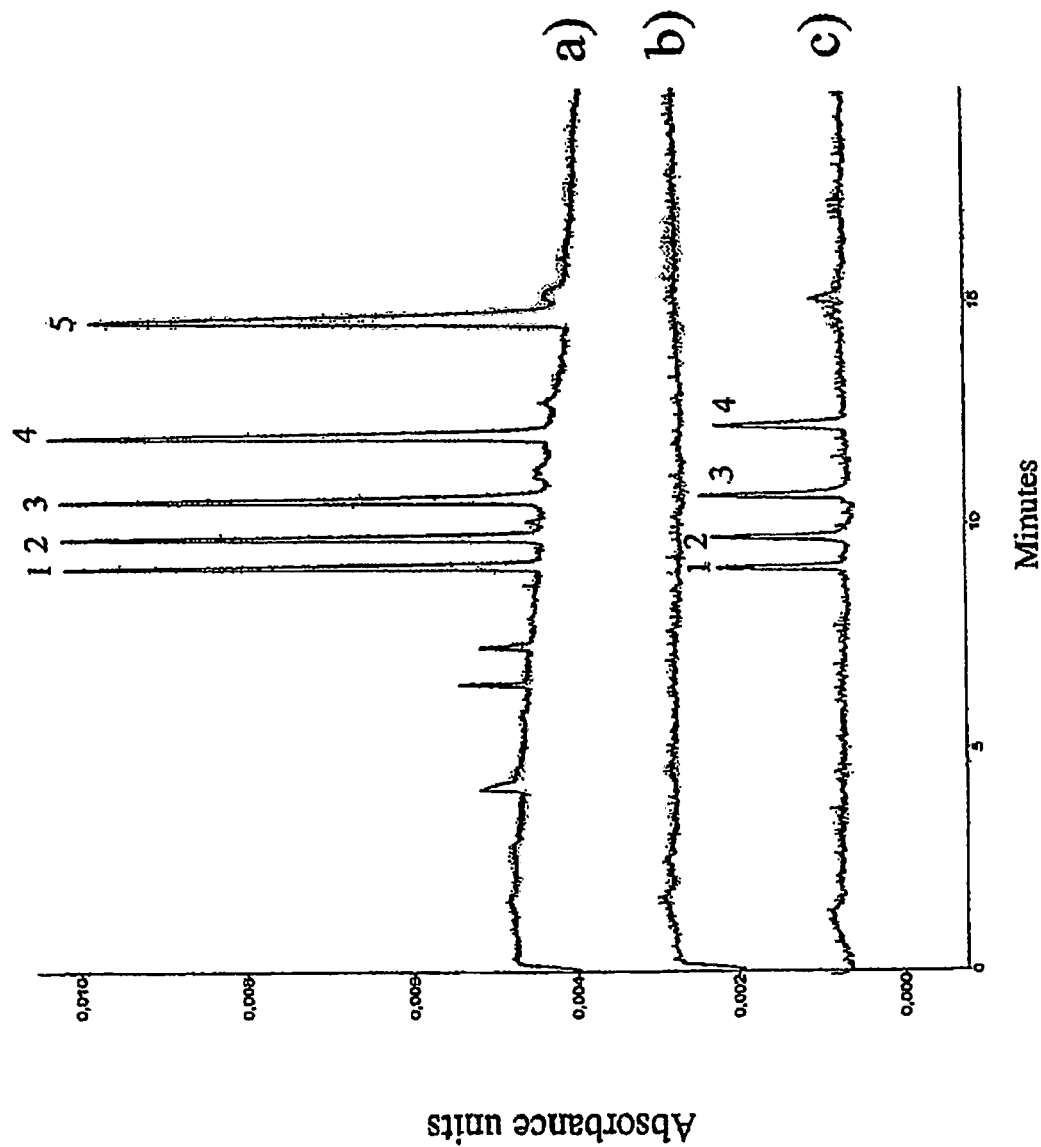
FIG. 3. Electropherograms demonstrating the strong effect of voltage on cross-membrane transport: a) acceptor phase after 5 minutes of ECMI at 300 V, b) acceptor phase after 5 minutes of extraction with no voltage and with pH 2 in both the sample solution and in the acceptor, and c) acceptor phase after 5 minutes of extraction with no voltage and with pH 13 in the sample solution and pH 2 in the acceptor.

In FIG. 3, an electropherogram of the acceptor solution after 5 minutes of ECMI at 300 V is shown. This figure demonstrates that five model analytes, pethidine, nortriptyline, methadone, haloperidol and loperamide, were effectively transported across the artificial liquid membrane and trapped in the acceptor solution as an electrical potential difference was applied. Recovery values were in the range 70 to 79%. In a second experiment (FIG. 3b), the operation was repeated without application of the voltage. In this case, the only driving force for cross-membrane transport was passive diffusion, and this resulted in no detectable peaks. Clearly, the electrical potential difference was the driving force in ECMI, whereas passive diffusion was undetectable. In another experiment without voltage, pH in the sample solution was adjusted to approximately 13 to deionize the model analytes, and the reason for this was to optimize their cross-membrane transport by passive diffusion.[25] An electropherogram from this experiment is shown in FIG. 3c. In this case, recovery values for four of the model analytes ranged between 18 and 26%, whereas loperamide was not detected. This experiment demonstrated that even if the conditions were optimized for cross-membrane transport based on passive diffusion, this process was significantly less effective than cross-membrane transport based on electrokinetic migration with an electrical potential difference. In other words, ECMI appears to be a very rapid isolation technique capable of high analyte recoveries.

Agitation of the whole system was found to be important for the cross-membrane transport. With no agitation, recovery values for the five model drugs were in the range 8-10%, whereas they were improved to 70 to 79% as mentioned above when agitation at 1200 rpm was performed. This agitation speed was the maximum value obtainable with the current agitation system used.

Theoretical Understanding.

Without wishing to be bound by theory, the inventors consider the following to be the theoretical basis of the present inventive concept: In order to enable ECMI, the whole system comprising the sample solution, the artificial liquid membrane, and the acceptor solution should serve as an electrical circuit. The major electrical resistance of the system was focused in the artificial liquid membrane, and the solvent used here was critical in order to ensure penetration of the electrical energy. Thus, a solvent with a certain polarity or water content should be used to give sufficient electrical conductance, and to ensure penetration of the electrical field. Basically, the cross-membrane transport of model analytes increased with decreasing electrical resistance of the artificial liquid membrane. However, provided that the artificial liquid membrane and the model analytes were inert to electrode reactions, the following electrode processes occurred in the sample and acceptor solutions, respectively:

Sample solution: $H_2O \rightarrow 2H^+ + 1/2O_2 + 2e^-$

Acceptor solution: $2H^+ + 2e^- \rightarrow H_2$

Thus, $O_2$ and $H_2$ were generated at the two electrodes, and this bubble formation increased with increasing current flow in the system (decreasing electrical resistance of the artificial liquid membrane). In other words, in order to suppress substantial bubble formation, the electrical conductance of the artificial liquid membrane should not be too high, but rather a compromise between the transport efficiency and the bubble formation tendency. 2-Nitrophenyl octyl ether among others appeared to be a successful compromise in terms of electrical conductance, and with this solvent, no deteriorating bubble formation was observed during visual inspection.

EXAMPLE

Basic Analytes

In the sample solution, pH was adjusted into the acidic range to ensure that the basic model analytes (B) were totally protonated ($BH^+$). Upon application of the electrical potential difference, the protonated model analytes started their electrokinetic migration from the sample solution, and in the direction towards the negative electrode placed in the acceptor solution. In the aqueous sample solution, the electrical field strength (V/cm) was relatively low due to the low electrical resistance of this phase, but nevertheless, because the model analytes were totally protonated, they rapidly migrated towards the artificial liquid membrane. This rapid migration was also promoted by using a thin sample vial which ensured a short migration distance to the artificial membrane. The different model analytes migrated with different velocity in the sample solution based on their charge-to-size ratio, but this was expected only to be a minor factor responsible for the differences observed in their individual transport efficiencies (recovery values).

Secondly, the model analytes crossed the interface to the artificial liquid membrane. In this phase, the electrical field strength (V/cm) was high due to the high electrical resistance of the organic solvent used. In spite of this, their electrokinetic migration was strongly suppressed in this medium because deprotonation of the basic substances occurred in the non-polar medium. In other words, the migration inside the artificial liquid membrane was strongly controlled by the following equilibrium:

$BH^+ \leftrightarrow B + H^+$

For compounds with a low degree of deprotonation, the electrokinetic migration through the artificial membrane was relatively high, whereas strongly deprotonating compounds showed very low electrokinetic migration and were effectively discriminated by the artificial liquid membrane. This phenomenon was expected to be the principal reason for the differences in extraction recoveries observed. In addition, differences in the charge-to-size ratios were also expected to affect the individual transport efficiencies in the artificial liquid membrane.

Optimization of the Organic Phase.

In order to further investigate the ECMI system, experiments with different organic solvents as the artificial liquid membrane were conducted to optimize this part of the system. The results for experiments conducted with the 5.2 mm vials are summarized in Table 1. As pure solvents, 2-nitrophenyl octyl ether, dihexyl ether, 1-octanol, 2-octanone, and dodecyl acetate were tested as ECMI candidates. 2-nitrophenyl octyl ether provided high recoveries (70 to 79%) for all the model analytes, 1-octanol resulted in low recoveries (3-7%), whereas no analyte transport was observed through dihexyl ether and dodecyl acetate. With 2-octanone, electrokinetic migration was observed in some cases, but the results were unreliable with a large standard deviation. In order to improve the electrical conductance of the artificial liquid membrane, 5% di(2-ethylhexyl)phosphate was added to 2-nitrophenyl octyl ether, but this resulted in decreased recoveries as compared with pure 2-nitrophenyl octyl ether.

In addition to pure solvents, we also tested some different commercial oils as the artificial liquid membrane as shown in Table 1. Kerosene, silicon oil (phenyl-methyl polysiloxane), and soy-bean oil all failed and provided no electrokinetic migration of the model analytes, whereas high recoveries were observed for 4 of the model analytes based on the use of peppermint oil. Thus, peppermint oil appeared to be an interesting green-chemistry alternative to 2-nitrophenyl octyl ether. Because 2-nitrophenyl octyl ether provided high recovery for the entire model analytes studied, this solvent was used as the artificial liquid membrane through the rest of this work.

In a second experiment the sample donor solution contained the following 7 organic compounds in a concentration of 1 μg/ml: amphetamine, methamphetamine, pethidine, nortriptylin, methadone, haloperidol and loperamide. Interestingly, the recovery for methamphetamine was only 11%, whereas the recovery for the closely related compound amphetamine was below 1%. Both compounds are slightly more hydrophilic than the drug substances discussed above, and this indicates that electrokinetic migration across the NPOE membrane was highly selective.

In a third experiment, the NPOE membrane was modified with the conductivity improving agents 5% (w/w) di(2-ethylhexyl)phosphate (DEHP) and 10% (w/w) tris(2-ethylhexyl)phosphate (TEHP). With this membrane, amphetamine and methamphetamine were effectively recovered in the acceptor solution with recovery values of 85 and 77 respectively after 5 minutes of operation. On the other hand, the more hydrophobic substances were now discriminated, and their recovery values dropped significantly. In a fourth experiment, 6 hydrophilic drugs: hydralazine, metaraminol, cimetidine, sotalol, practolol and atenolol were added to the donor solution, so that it contained each of them in a concentration of 1 μg/ml. With NPOE and NPOE modified with 5% DEHP and 10% TEHP, no recovery was observed for the hydrophilic drugs. However, with a 1:1 (w/w) mixture of NPOE and DEHP, the hydrophilic drugs were effectively recovered in the acceptor solution with recovery values between 14 and 73%. Thus, migration across the liquid membrane was highly selective, and the selectivity was easily adjusted by chemical modifications of the liquid membrane.

As a further example of variation of the organic phase of the liquid membrane, Table 5 summarizes experiments conducted in the 7 mm vials and demonstrates that polar basic drugs are poorly extracted with pure 2-nitrophenyl octyl ether as the organic phase, whereas addition of di-(2-ethylhexyl) phosphate provided an efficient organic phase for the extraction of polar basic drugs. This finding suggests that the chemistry of the organic phase may be varied to address different type of analytes.

Table 6 summarizes the effect of addition of tris-(2-ethylhexyl)phosphate (TEHP) to the organic phase (2-nitrophenyl octyl ether) and supports Table 5. Table 7 demonstrates that addition of both di-(2-ethylhexyl)phosphate and tris-(2-ethylhexyl)phosphate (TEHP) to the organic phase (2-nitrophenyl octyl ether) may give an organic phase capable of extracting both non-polar and polar basic drugs simultaneously.

Optimization of pH in the Acceptor Solution.

In a second series of experiment for basic analytes, different types of acceptor solutions were evaluated for ECMI performance. The results are summarized in Table 2, and indicated that 10 mM HCl provided the highest recoveries. As the concentration of HCl was decreased, the recoveries decreased. Interestingly, also 10 mM formic acid served as an efficient acceptor solution providing results comparable with HCl. Although 10 mM HCl was used during the rest of this work, formic acid may be highly interesting in combination with LC-MS, and for applications where the analytes are unstable in strongly acidic solutions. Different phosphate buffers with pH in the range 6.0 to 8.0 were also tested, but these showed poor performance. With increasing pH, the electrokinetic migration into the acceptor solution was reduced due to partial deprotonation of the model analytes, and back-diffusion based on passive transport from the acceptor to the sample solution was accelerated for the same reason.

Optimization of pH in the Sample.

In a third experiment for basic analytes, different acid solutions and buffer solutions were tested as sample, and in all cases, the model analytes were spiked into these solutions to a constant concentration level. The results are summarized in Table 3. As seen from the table, all the different sample solution provided relatively high recoveries, which indicated that pH in the sample was not highly critical for the ECMI process. Surprisingly, even the phosphate buffer at pH 8.0 gave high recoveries, even if the pH value in this case was close to the $pK_a$-values for several of the basic model analytes. Most probably, this supported the theoretical discussion above that electrokinetic migration in the sample, which was reduced at pH 8.0 due to deprotonation of the model analytes, was not the limiting step controlling the cross-membrane transport, and that transport limitations in the system was associated with the artificial liquid membrane. For the rest of this work, 1.0 mM HCl was utilized as the sample compartment.

Optimization of Time and Voltage.

Figure 4:
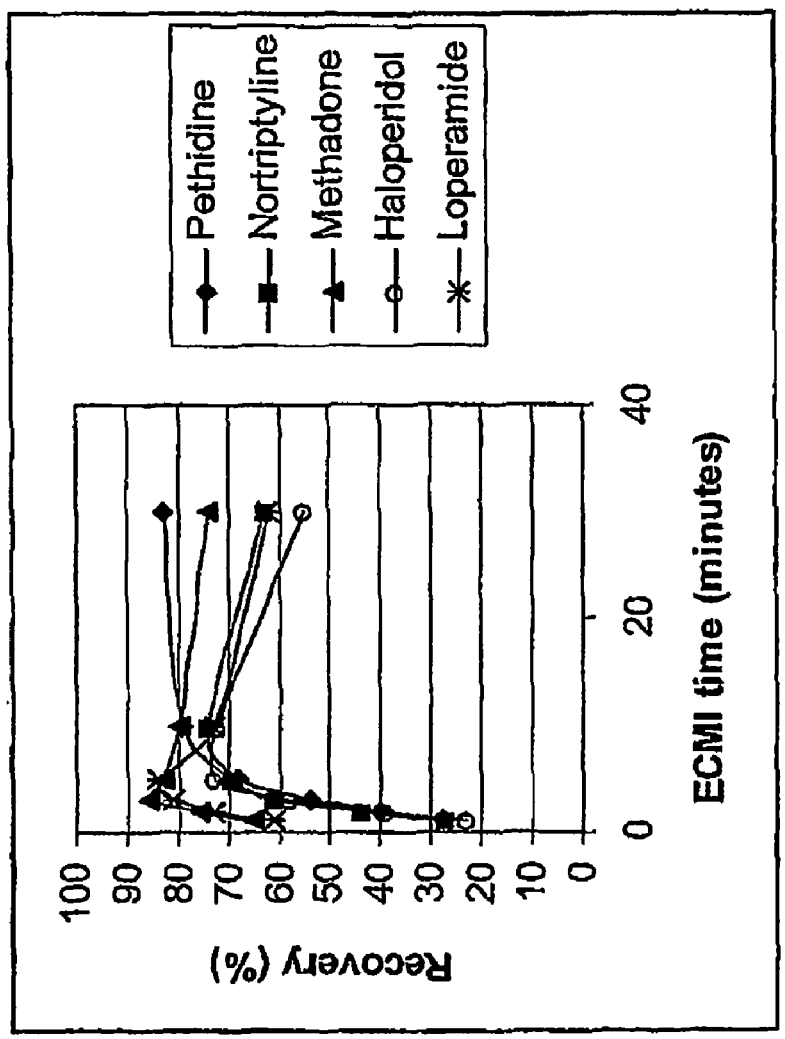
FIG. 4. Effect of time on cross-membrane transport.

In order to continue the optimization of ECMI, recovery of the different model analytes was studied as function of ECMI time. The results are summarized in FIG. 4. In general, recoveries increased with increasing ECMI time up to 5 minutes, where after recoveries leveled off or even decreased with increasing ECMI time. The reason for the level off effect was, as mentioned earlier, that electrokinetic migration was balanced by back-diffusion to the sample solution due to reversal of the concentration gradient. The slight decrease in recoveries after long time ECMI probably was due to experimental inaccuracies or due to a small loss of artificial liquid membrane. Recoveries for methadone and loperamide Increased very rapidly with extraction time, whereas the other model analytes responded more slowly. Most probably, the observed behavior of the latter was a result of a relatively strong stability of their protonated species within the artificial liquid membrane, which in turn resulted in superior electrokinetic migration. A similar experiment on recovery versus time was conducted for transport based on passive diffusion only, without applying the electrical potential difference and adjusting pH in the sample to approximately 12. In this case 30 to 45 minutes of extraction was required before extraction recoveries leveled off. Thus, the speed of transport across the artificial liquid membrane was improved dramatically upon application of the electrical potential difference. During the rest of this work, 5 minutes was selected as ECMI time.

Figure 5:
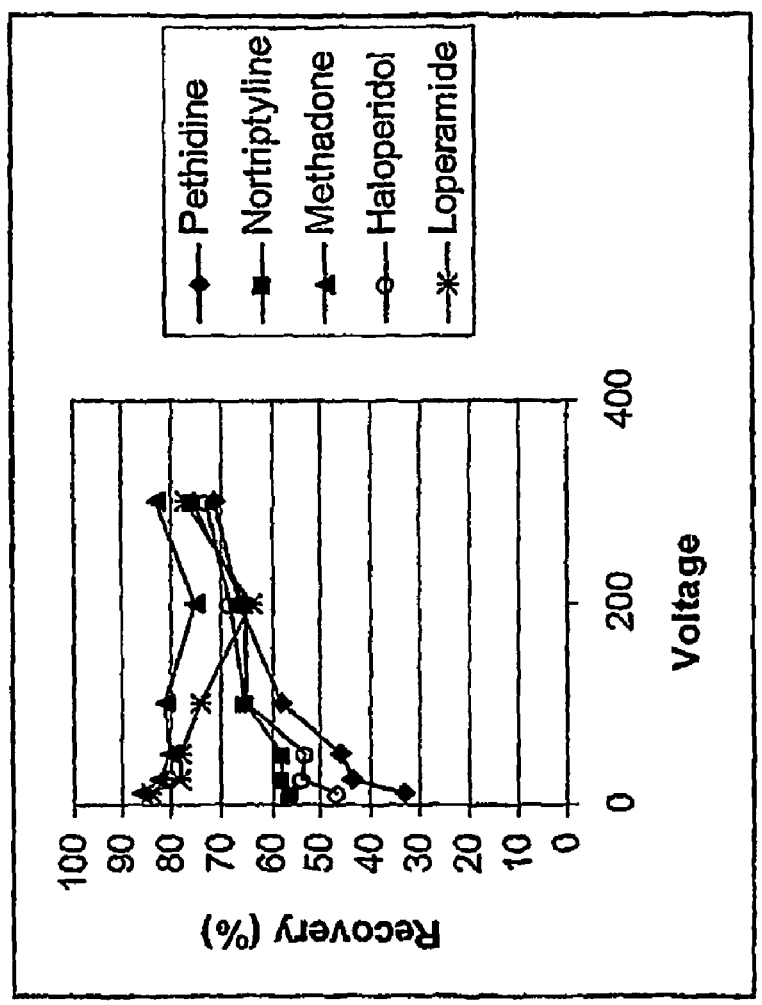
FIG. 5. Effect of voltage on cross-membrane transport.

In another experiment, recoveries were investigated as a function of the applied electrical potential difference. These results are demonstrated in FIG. 5. For pethidine, haloperidol, and nortriptyline, relatively high recoveries were obtained with only 10 V as the potential difference, but recoveries increased further as the voltage was increased up to the upper limit at 300 V for the power supply. In their protonated form, the stability in the artificial liquid membrane was relatively poor, and high electrical potential differences were required to promote efficient migration through the artificial membrane. For methadone and loperamide in contrast, the highest recovery was obtained at 10 V, whereas recoveries decreased slightly as the applied voltage was increased up to 300 V. The latter compounds most probably showed higher stability as protonated species in the artificial liquid membrane, and consequently, lower electrical potential differences were required for effective electrokinetic migration. During the rest of this work, 300 V was used as the potential difference.

Table 9 demonstrates that extractions may also performed at very low potentials (1. V) with nitrobenzene as the organic phase. There may be several advantages of running the process at low voltages rather than at 300 V.

Performance Characteristics and Validation.

On the basis of the experiments discussed above, optimal ECMI of the model analytes was obtained utilizing 2-nitrophenyl octyl ether as the artificial liquid membrane, an acceptor solution of 10 mM HCl, a sample solution containing 10 mM HCl, 300 V potential difference, and 5 minutes of ECMI time. In this case, the model analytes were transferred to the acceptor solution with 70 to 79% recoveries. Since the model analytes were transferred from a 300 µl sample volume to a 30 µl acceptor phase solution, the corresponding enrichment (E) ranged between 7.0 and 7.9.

To evaluate the practical applicability of the proposed ECMI technique, repeatability and linearity were investigated utilizing standard solutions of the model analytes in 10 mM HCl. In a first experiment, the repeatability was studied (n=6) at two different concentration levels (100 ng/ml and 1000 ng/ml). As illustrated in Table 4, relative standard deviations were in the range 4.6-10.5% at the 100 ng/ml level, and in the range 5.4-16.0% at the 1000 ng/ml level. The repeatability was acceptable and comparable with values reported for miniaturized analytical extraction procedures.[25]

As a final preliminary validation, ECMI of 1 µg/ml of methadone was accomplished from 1) pure 10 mM HCl, 2) 10 mM HCL containing 10 µg/ml pethidine, and 3) 10 mM HCl containing 2% (w/w) NaCl. The corresponding recovery values for methadone were 77, 80, and 83%, and within the experimental inaccuracies of the experiment, ECMI of methadone was not found to be affected by the presence of the aforementioned matrix components.

Table 8 demonstrates analytical validation data for polar and non-polar drugs, supporting that the concept may be used for analytical purposes.

Compatibility with Biological Samples.

Figure 6:
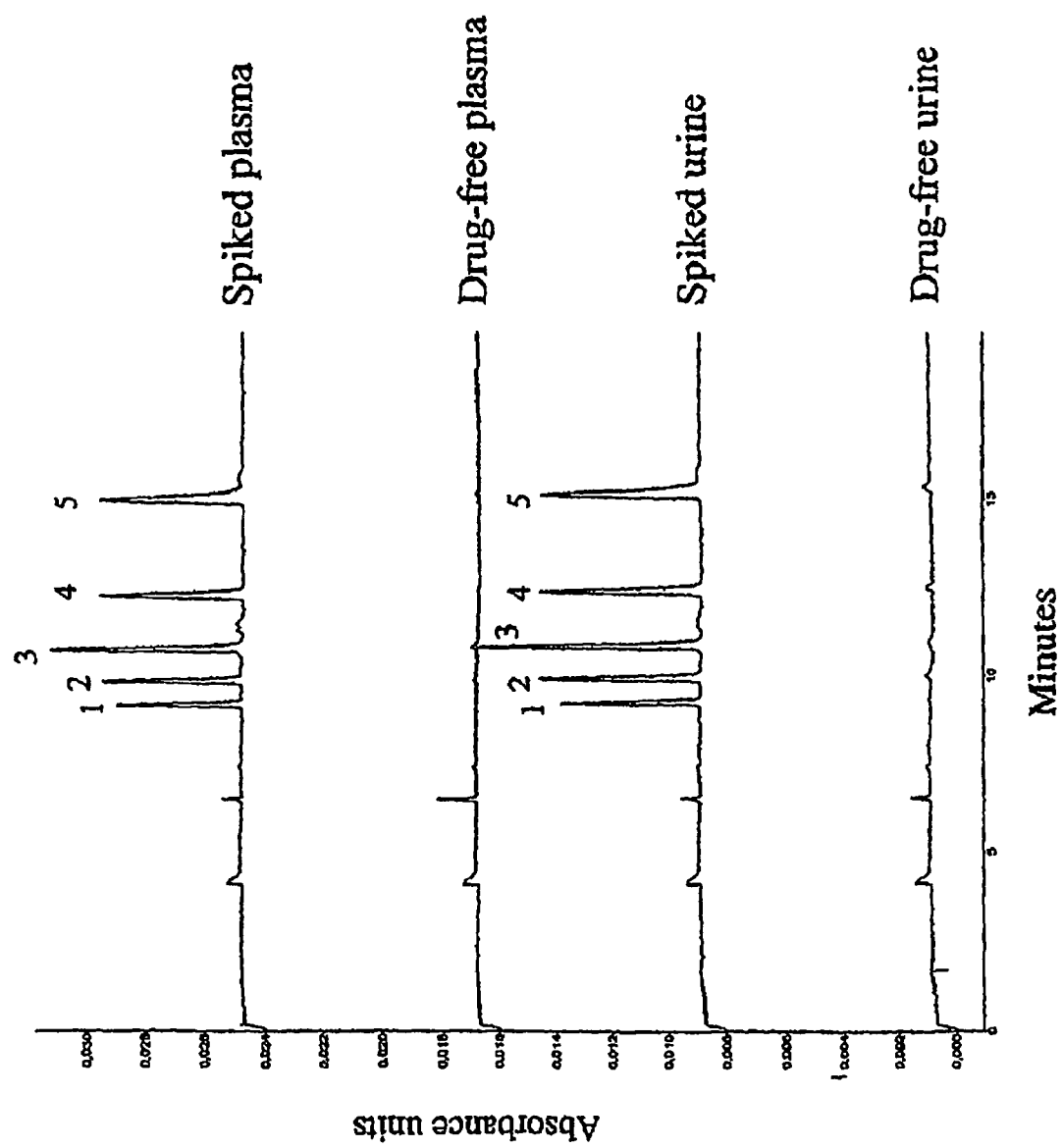
FIG. 6. ECMI from human plasma and urine.
Figure 7:
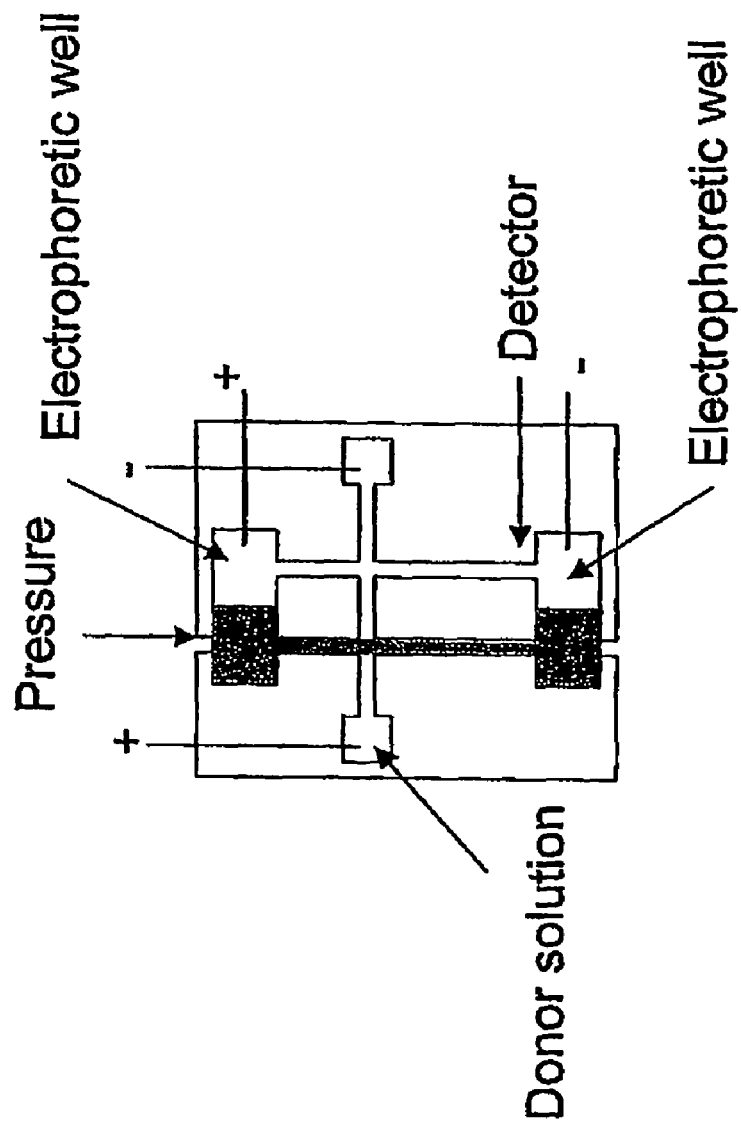
FIG. 7: Schematic illustration of an embodiment wherein a device according to this invention is incorporated into a micro-chip analysing unit.
Figure 8:
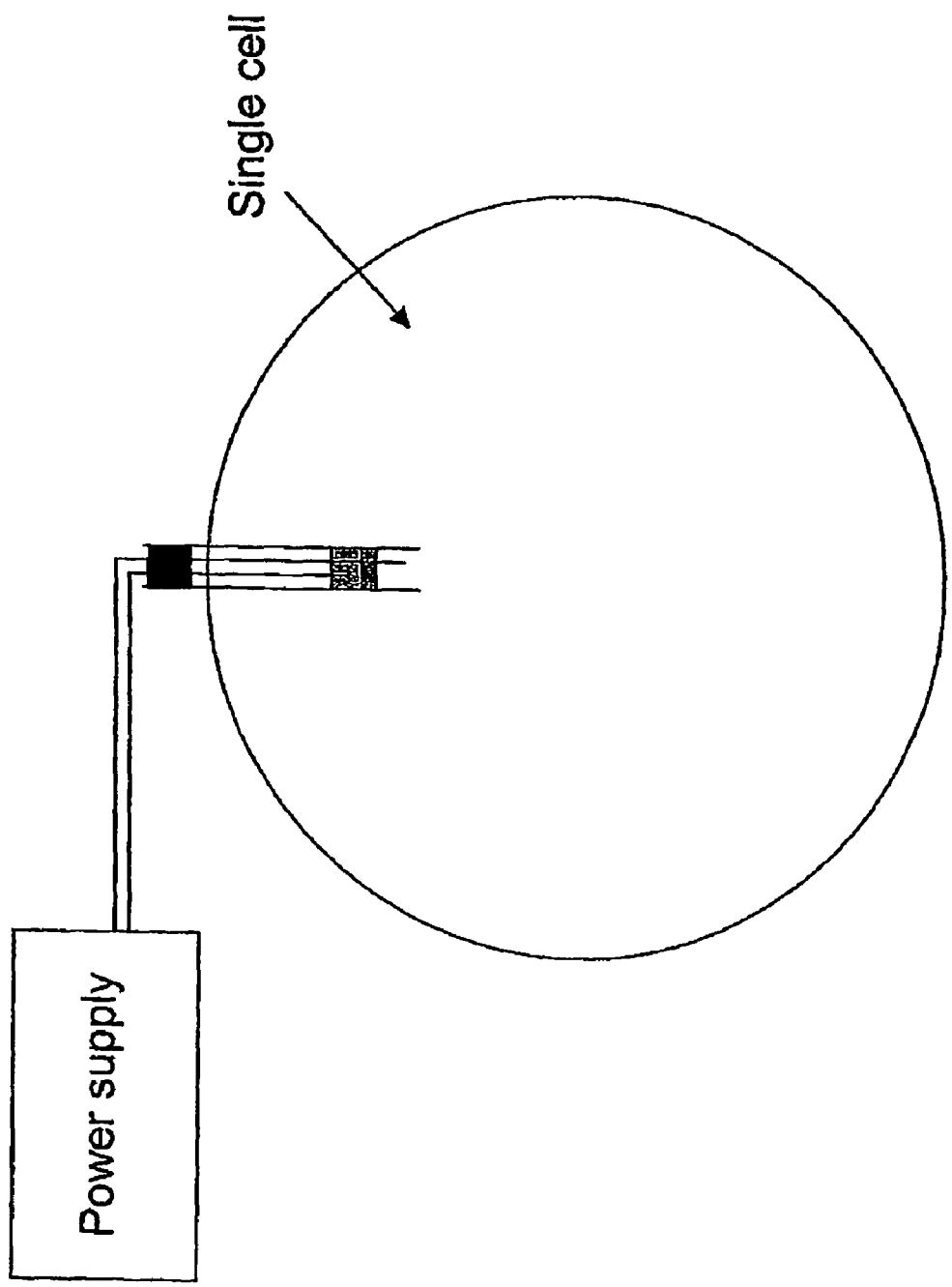
FIG. 8: Schematic illustration of a device according to this invention for use in extraction directly from a single cell.

To finish the evaluation of ECMI, the model analytes were spiked into samples of human blood plasma and urine. In both cases, 100 μl of biological fluid was mixed with 200 μl of 15 mM HCl to give a final concentration of 10 mM HCl in the sample compartment. Subsequently, the samples were subjected to ECMI with the same conditions as reported above. FIG. 6 demonstrates the electropherograms obtained after analysis of the resulting acceptor solutions. Clearly, the model analytes were effectively extracted even from biological samples, and the system was found to be compatible with the complicated samples. The results from urine were comparable with similar results from pure sample solutions of 10 mM HCl. Thus, in the case of urine, the sample matrix was found not to affect the recoveries obtained. Also for plasma, recoveries were comparable with similar results from pure sample solutions of 10 mM HCl, except for nortriptyline where plasma experiments resulted in slightly lower recoveries. Most probably, this arose from the protein binding of the drug.

Interestingly, very few matrix components were observed in the corresponding electropherograms of drug-free plasma and urine. This supported that the majority of endogenous substances were effectively discriminated or blocked by the artificial liquid membrane, and in turn suggests that ECMI may be a highly selective sample preparation method producing very clean extracts.

Extraction of Acidic Drugs

The device and method of the present invention may be applied to any organic compounds capable of being partly or completely ionized. Thus, for acidic drugs alkaline conditions in the sample and acceptor solutions are preferred. The sample solution was made alkaline to pH 12 with NaOH. A negative electrode was placed in the sample solution and connected to the power supply. The porous hollow fibre was dipped in n-octanol for 5 seconds to Immobilize the solvent in the pores of the fibre and 10 mM NaOH as acceptor solution was added to the lumen of the fibre. The hollow fibre was placed in the sample and the positive electrode was placed in the lumen of the fibre. The positive electrode was connected to the power supply and a potential of 15V was applied over the electrodes for 5 min. Table 10 demonstrates the successful extraction of acidic compounds.

Conclusions

The present invention has for the first time demonstrated that electrokinetic migration across thin artificial liquid membranes may be a very powerful concept for isolation, enrichment, and purification of drug substances from complicated biological samples. This technique has been named electrokinetic cross-membrane isolation (ECMI). Compared with passive diffusion, electrokinetic migration appeared to be a much more efficient transport mechanism, providing high analyte recoveries in very short time. ECMI was found to be compatible with complicated biological samples like human plasma and urine, and preliminary validation data supported that this concept may be utilized as a sample preparation technique for analytical measurements. The sample preparation method of the present invention provides a very rapid, simple, and selective isolation of chemical and biochemical substances from complicated samples with almost no consumption of organic solvents.

TABLE 1

Recovery with different organic liquid membranes
Recovery (%)[a]

| | Pethidine | Nortriptyline | Methadone | Haloperidol | Loperamide |
|---|---|---|---|---|---|
| 2-nitrophenyl octyl ether | 70 | 70 | 79 | 72 | 76 |
| Dihexyl ether | nd | nd | nd | nd | nd |
| 1-Octanol | 3 | 4 | 7 | 3 | 7 |
| 2-Octanone | * | * | * | * | * |
| Dodecylacetate | nd | nd | nd | nd | nd |
| 2-nitrophenyl octyl ether + 5% di(2-ethylhexyl) phosphate | 57 | 13 | 26 | 3 | 4 |
| Kerosene | nd | nd | nd | nd | nd |
| Silicone oil AS 4 | nd | nd | nd | nd | nd |
| Soy-bean oil | nd | nd | nd | nd | nd |
| Peppermint oil | 13 | 73 | 73 | 78 | 79 |

[a] (n = 3), relative standard deviations were all below 15% RSD
* Recovery was observed, but results were unreliable due to large standard deviations

TABLE 2

Recovery with different acceptor solutions
Recovery (%)[a]

| | Pethidine | Nortriptyline | Methadone | Haloperidol | Loperamide |
|---|---|---|---|---|---|
| 100 mM HCl | 60 | 40 | 83 | 72 | 80 |
| 10 mM HCl | 70 | 70 | 79 | 72 | 76 |
| 1 mM HCl | 44 | 27 | 31 | 23 | 22 |
| 10 mM HCOOH | 56 | 70 | 63 | 52 | 61 |
| 10 mM phosphate pH 6.0 | 24 | 24 | 26 | 9 | 15 |
| 10 mM phosphate pH 7.0 | 19 | 8 | 9 | nd | 4 |
| 10 mM phosphate pH 8.0 | nd | nd | nd | nd | nd |

[a] (n = 3), relative standard deviations were all below 15% RSD

TABLE 3

Recovery with different compositions of the sample solution
Recovery (%)[a]

| | Pethidine | Nortriptyline | Methadone | Haloperidol | Loperamide |
|---|---|---|---|---|---|
| 100 mM HCl | 72 | 65 | 78 | 65 | 68 |
| 10 mM HCl | 70 | 70 | 79 | 72 | 76 |
| 1 mM HCl | 64 | 59 | 71 | 63 | 65 |
| 10 mM HCOOH | 68 | 69 | 76 | 69 | 73 |
| 10 mM phosphate pH 6.0 | 61 | 57 | 73 | 58 | 57 |
| 10 mM phosphate pH 7.0 | 63 | 62 | 71 | 58 | 49 |
| 10 mM phosphate pH 8.0 | 63 | 60 | 72 | 60 | 50 |

[a](n = 3), relative standard deviations were all below 15% RSD

TABLE 4

ECMI performance and validation data

| | Pethidine | Nortriptyline | Methadone | Haloperidol | Loperamide |
|---|---|---|---|---|---|
| Recovery (%) | 70 | 70 | 79 | 72 | 76 |
| Enrichment | 7.0 | 7.0 | 7.9 | 7.2 | 7.6 |
| Repeatability (n = 6) 100 ng/ml | 9.5 | 6.0 | 4.6 | 5.5 | 10.5 |
| Repeatability (n = 6) 1000 ng/ml | 9.3 | 16.0 | 13.1 | 10.1 | 5.4 |

TABLE 5

Addition of di-(2-ethylhexyl) phosphate (DEHP) to the organic phase (2-nitrophenyl octyl ether).

Conditions

| Sample: | 300 µl water sample acidified to pH 2.0 with HCl |
|---|---|
| Organic phase: | See table |
| Acceptor phase: | 30 µl 10 mM HCl |
| Voltage: | 300 V |

| | | | | Recovery (%)[2] DEHP-content % (w/w) | | | | |
|---|---|---|---|---|---|---|---|---|
| Compound | log P[1] | pK$_a$[1] | Mw | 0% | 5% | 10% | 25% | 50% |
| Practolol | −1.3 | 9.5 | 266.3 | nd | 3 | 9 | 27 | 30 |
| Metaraminol | −0.3 | 8.6 | 167.2 | nd | nd | nd | 6 | 7 |
| Sotalol | 0.2 | 8.2, 9.8 | 272.4 | nd | 7 | 16 | 29 | 23 |
| Atenolol | 0.2 | 9.6 | 266.3 | nd | 9 | 18 | 38 | 37 |
| Cimetidine | 0.4 | 6.8 | 252.4 | nd | 13 | 22 | 39 | 30 |
| Hydralazine | 1.0 | 0.5, 7.1 | 160.2 | nd | 59 | 54 | 75 | 71 |
| Nortriptyline | 1.7 | 9.7 | 263.4 | 33 | 2 | 2 | nd | — |
| Amfetamine | 1.8 | 10.1 | 135.2 | nd | 30 | 38 | 24 | — |
| Metamfetamine | 2.1 | 10.1 | 149.2 | nd | 31 | 30 | 12 | — |
| Methadone | 2.1 | 8.3 | 309.4 | 78 | 5 | 9 | 4 | — |
| Hydroxyzine | 2.4 | 2.1, 7.1 | 374.9 | 69 | nd | 3 | nd | — |
| Pethidine | 2.7 | 8.7 | 247.3 | 16 | 30 | 33 | 9 | — |
| Mepyramine | 2.8 | 4.0, 8.9 | 285.4 | 64 | 53 | 20 | 9 | — |
| Promethazine | 2.9 | 9.1 | 284.4 | 59 | nd | nd | nd | — |
| Haloperidol | 3.2 | 8.3 | 375.9 | 53 | nd | nd | nd | — |
| Fluphenazine | 3.5 | 3.9, 8.1 | 437.5 | 24 | 10 | nd | nd | — |
| Phencyclidine | 4.7 | 8.5 | 243.3 | 83 | 13 | nd | nd | — |
| Clomipramine | 5.2 | 9.5 | 314.9 | 67 | nd | nd | nd | — |
| Loperamide | 5.2 | 8.1 | 477.0 | 73 | nd | — | nd | — |
| Clemastine | 5.7 | 10.2 | 343.9 | 73 | — | — | — | — |

[1]Clarkes Analysis of Drugs and Poisons, A. C. Moffat, M. D. Osselton, B. Widdop, Third edition, Pharmaceutical Press, London, UK
[2]Based on 4 replicates

TABLE 6

Addition of tris-(2-ethylhexyl) phosphate (TEHP) to the organic phase (2-nitrophenyl octyl ether).

Conditions

| Sample: | 300 µl water sample acidified to pH 2.0 with HCl |
|---|---|
| Organic phase: | See table |
| Acceptor phase: | 30 µl 10 mM HCl |
| Voltage: | 300 V |

| | Recovery (%)[1] | | |
|---|---|---|---|
| Compound | 0% | 5% | 10% |
| Practolol | nd | nd | nd |
| Metaraminol | nd | nd | nd |
| Sotalol | nd | nd | nd |
| Atenolol | nd | nd | nd |
| Cimetidine | nd | nd | nd |
| Hydralazine | nd | nd | nd |
| Nortriptyline | 33 | 78 | 76 |
| Amfetamine | nd | 17 | 44 |
| Metamfetamine | nd | 53 | 72 |
| Methadone | 78 | 91 | 80 |
| Hydroxyzine | 69 | 70 | 61 |
| Pethidine | 16 | 78 | 88 |
| Mepyramine | 64 | 54 | 49 |
| Promethazine | 59 | 58 | 53 |
| Haloperidol | 53 | 83 | 79 |
| Fluphenazine | 24 | 31 | 33 |
| Phencyclidine | 83 | 71 | 95 |
| Clomipramine | 67 | 59 | 54 |
| Loperamide | 73 | 53 | — |
| Clemastine | 73 | — | — |

[1]Based on 4 replicates

TABLE 7

Addition of di-(2-ethylhexyl) phosphate (DEHP) and tris-(2-ethylhexyl) phosphate (TEHP) to the organic phase (2-nitrophenyl octyl ether).

Conditions

| | |
|---|---|
| Sample: | 300 µl water sample acidified to pH 2.0 with HCl |
| Organic phase: | See table |
| Acceptor phase: | 30 µl 10 mM HCl |
| Voltage: | 300 V |

| | Recovery (%)[1] | | |
|---|---|---|---|
| Compound | 0% DEHP + 0% TEHP | 10% DEHP + 10% TEHP | 25% DEHP + 25% TEHP |
| Practolol | nd | 10 | 16 |
| Metaraminol | nd | 6 | 14 |
| Sotalol | nd | 26 | 27 |
| Atenolol | nd | 21 | 26 |
| Cimetidine | nd | 23 | 26 |
| Hydralazine | nd | 44 | 35 |
| Nortriptyline | 33 | 7 | 10 |
| Amfetamine | nd | 69 | 78 |
| Metamfetamine | nd | 64 | 60 |
| Methadone | 78 | 39 | 25 |
| Hydroxyzine | 69 | — | 14 |
| Pethidine | 16 | 61 | 63 |
| Mepyramine | 64 | 55 | 53 |
| Promethazine | 59 | — | 4 |
| Haloperidol | 53 | 5 | 4 |
| Fluphenazine | 24 | — | 41 |
| Phencyclidine | 83 | 43 | 23 |
| Clomipramine | 67 | — | 1 |
| Loperamide | 73 | nd | 4 |
| Clemastine | 73 | 43 | 23 |

[1]Based on 4 replicates

TABLE 8

Validation data for polar drugs.

Conditions

| | |
|---|---|
| Sample: | 300 µl water sample acidified to pH 2.0 with HCl |
| Organic phase: | See table |
| Acceptor phase: | 30 µl 10 mM HCl |
| Voltage: | 300 V |

| | Repeatability % RSD (n = 6) | | Linearity (r²) |
|---|---|---|---|
| | 250 ng/ml | 1000 ng/ml | (250 ng/ml-5 µg/ml) |
| Practolol[1] | 18 | 14 | 0.9978 |
| Sotalol[1] | 20 | 13 | 0.9988 |
| Atenolol[1] | 15 | 13 | 0.9984 |
| Cimetidine[1] | 9 | 9 | 0.9969 |
| Hydralazine[1] | 15 | 10 | 0.9972 |
| Promethazine[2] | 20 | 14 | 0.9985 |
| Clomipramine[2] | 13 | 14 | 0.9976 |

[1]Performed with 25% (w/w) DEHP in 2-nitrophenyl octyl ether as the organic phase
[2]Performed with pure 2-nitrophenyl octyl ether as the organic phase

TABLE 9

Extraction at low potentials.

Conditions

| | |
|---|---|
| Sample: | 300 µl water sample acidified to pH 2.0 with HCl |
| Organic phase: | See table |
| Acceptor phase: | 30 µl 10 mM HCl |
| Voltage: | 1 V |

| | Recovery (%) | | |
|---|---|---|---|
| Compound | Nitrobenzene | 1-Isopropyl Nitrobenzene | 2-Nitrophenyl octyl ether |
| Amphetamine | nd | nd | nd |
| Metamphetamine | 7 | 26 | nd |
| Pethidine | 28 | nd | nd |
| Nortriptyline | 43 | 3 | 1 |
| Methadone | 50 | 27 | 8 |
| Haloperidol | 40 | 6 | 1 |
| Loperamide | 16 | 36 | 8 |

TABLE 10

Extraction of acidic compounds

Conditions

| | |
|---|---|
| Sample: | 300 µl water made alkaline to pH 12.0 with NaOH |
| Organic phase: | n-octanol |
| Acceptor phase: | 30 µl 10 mM NaOH |
| Voltage: | 15 V |

| Compound | Recovery (%) |
|---|---|
| Ibuprofen | 49% |
| Naproxen | 64% |

LITERATURE REFERENCES (1) Cox, J. A.; Carlson, R. *Anal. Chim. Acta* 1981, 130, 313.
(2) Debets, A. J. J.; Kok, W. Th.; Hupe, K.-P.; Brinkman, U. A. Th. *Chromatographia* 1990, 30, 361.
(3) Buscher, B. A. P.; Tjaden, U. R.; van der Greef, J. *J. Chromatogr. A* 1997, 764, 135.
(4) Buscher, B. A. P.; Tjaden, U. R.; van der Greef, J. *J. Chromatogr. A* 1997, 788, 165.
(5) Levine, M. L.; Bier, M. *Electrophoresis* 1990, 11, 605.
(6) Clark, W. M. *Chemtech.* 1992, 22, 425.
(7) Marando, M. A.; Clark, W. M. *Sep. Sci. Technol.* 1993, 28, 1561.
(8) Thoes, C. W.; Clark, W. M. *Appl. Biochem. Biotechnol.* 1995, 54, 143.
(9) Theos, C. W.; Clark, W. M. *Appl. Biochem. Biotechnol.* 1995, 54, 143.
(10) Oehler, R. D.; Clark, W. M. *Biotechnol. Prog.* 1996, 12, 873.
(11) Zhal, S. L.; Luo, G. S.; Liu, J. G. *Chem. Eng. J.* 2001, 83, 55.
(12) Stichlmair, J.; Schmidt, J.; Proplesch, *Chem. Eng. Sci.* 1992, 47, 3015.
(13) Luo, G. S.; Yu, M. J.; Jiang, W. B.; Zhu, S. L.; Daí, Y. Y. *Sep Sci. Technol.* 1999, 34, 781
(14) Luo, G. S.; Jiang, W. B.; Lu, Y. C.; Zhu, S. L.; Daí, Y. Y. *Chem. Eng. J.* 1999, 73, 137.
(15) Luo, G. S.; Wu, F. Y.; *Sep. Sci. Technol.* 2000, 35, 2485.
(16) Luo, G. S.; Pan, S.; Liu, J. G.; Daí, Y. Y. *Sep. Sci. Technol.* 2001, 36, 2799.
(17) Pan, S.; Luo, G. S.; Liu, J. G.; Wang, J. D. *Sep. Sci. Technol.* 2003, 38, 3731.
(18) Luo, G. S.; Liu, J. G.; Lu, Y. C.; Pan, S.; Wang, J. D. *Sep. Sci. Technol.* 2004, 39, 1267.
(19) Luo, G. S.; Shan, X. Y.; QI, X.; Lu, Y. C. *Sep. Purif. Technol.* 2004, 38, 265.

(20) van der Vlis, E.; Mazereeuw, M.; Tjaden, U. R.; Irth, H.; van der Greef, J. *J. Chromatogr. A* 1994, 687, 333.
(21) van der Vlis, E.; Mazereeuw, M.; Tjaden, U. R.; Irth, H.; van der Greef, J. *J. Chromatogr. A* 1995, 712, 227.
(22) van der Vlis, E.; Mazereeuw, M.; Tjaden, U. R.; Irth, H.; van der Greef, J. *J. Chromatogr. A* 1996, 741, 13.
(23) Serga, V. E.; Kulikova, L. D.; Purin, B. A. *Sep. Sci. Technol.* 2000, 35, 299.
(24) Kullkova, L.; Petrichenko, O.; Serga, V.; Jansone, A. *J. Appl. Electrochem.* 2004, 34, 103.
(25) Pedersen-Bjergaard, S.; Rasmussen, K. E. *Anal. Chem.* 1999, 71, 2650.

The invention claimed is:

1. Device, comprising
a hydrophilic donor solution, having a pre-set pH, comprising at least one ionized or partially ionized organic compound, wherein the donor solution is mixture of an aqueous solution and a non-aqueous hydrophilic solution,
and a hydrophilic acceptor solution having a pre-set pH;
a liquid membrane comprising an immobilized organic solvent, which membrane is placed in fluid contact with both said donor solution and said acceptor solution so that it separates said donor solution and said acceptor solution, and through which organic solvent a current and said at least one ionized organic compound can traverse;
a first electrode to be placed in contact with the donor solution;
a second electrode to be placed in contact with the acceptor solution;
and a voltage source for applying a voltage over said electrodes.

2. Device according to claim 1, wherein said organic solvent is different from the solvent in said donor and/or acceptor solution.

3. Device according to claim 1, wherein the organic solvent of the liquid membrane is immiscible with the solvent of said donor and/or acceptor solutions.

4. Device according to claim 1, wherein the membrane thickness is in the range of 0.01-1000 µm.

5. Device according to claim 4, wherein the membrane thickness is in the range of 1-500 µm.

6. Device according to claim 4, wherein the membrane thickness is in the range of 5-50 µm.

7. Device according to claim 4, wherein the membrane thickness is in the range of 0.01-10 µm.

8. Device according to claim 1, further comprising a conductivity-improving additive in the organic solvent.

9. Device according to claim 1, wherein the membrane is a micro-porous hollow fibre.

10. Device according to claim 1, wherein the membrane is comprised of a polymeric film swollen with said organic solvent.

11. Device according to claim 1, wherein said organic compound belongs to the group consisting of pharmaceuticals, drugs, biological substances, organic pollutants, food additives, colours and poisons and metabolites of these.

12. Device according to claim 1, wherein said organic compound is chosen from the group consisting of, water-soluble, and fat-soluble and slightly water-soluble compounds.

13. Device according to claim 11, wherein the biological substance is chosen from the group consisting of DNA, proteins, peptides, amino acids, carbohydrates, lipids, polysaccharides, fatty acids and phospholipids.

14. Device according to claim 1, wherein the donor solution is a substantially aqueous solution.

15. Device according to claim 1, wherein a water miscible organic solvent is added to the donor solution in the range of 0.1-50% by weight.

16. Device according to claim 1, wherein the donor solution is a substantially non-aqueous solution comprising a hydrophilic organic solvent.

17. Device according to claim 1, wherein an aqueous solution or water is added to the donor solution in the range of 0.1-50% by weight.

18. Device according to claim 1, wherein the ratio aqueous solution:hydrophilic solution in the donor solution is in the range from 2:1 to 1:2.

19. Device according to claim 1, wherein the acceptor solution is a substantially aqueous solution.

20. Device according to claim 18, wherein a water-miscible organic solvent is added to the acceptor solution in the range of 0.1-50% by weight.

21. Device according to claim 1, wherein the acceptor solution is a substantially non-aqueous solution comprising a hydrophilic organic solvent.

22. Device according to claim 20, where in an aqueous solution or water is added to the acceptor solution in the range of 0.1-50% by weight.

23. Device according to claim 1, wherein the acceptor solution is a mixture of an aqueous solution and a non-aqueous hydrophilic solution.

24. Device according to claim 18, wherein the ratio aqueous solution:hydrophilic solution in the donor solution is 1:1.

25. Device according to claim 1, wherein the donor solution is comprised in a first compartment and the acceptor solution is comprised in a second compartment and the two compartments have relative volumes in the range donor compartment:acceptor compartment of 10,000:1 to 1:100.

26. Device according to claim 1, wherein the donor solution is comprised in a first compartment and the acceptor solution is comprised is a second compartment and the two compartments have relative volumes of 1:2 to 2:1.

27. Device according to claim 1, wherein the donor and acceptor solutions are placed in compartment(s) where at least one of said compartments are movable in relation to the other compartment and/or to the liquid membrane.

28. Device according to claim 1, which further comprises an agitating system for agitating at least one of said solutions.

29. Device according to claim 1, wherein the liquid membrane is a disposable liquid membrane.

30. Device according to claim 1, wherein the liquid membrane is a reusable liquid membrane.

31. Process for electrokinetic migration of an organic compound in a 3-phase system, comprising the steps of
providing a hydrophilic donor solution comprising at least one organic compound to be transferred from said donor solution to an acceptor solution;
adjusting the pH of said donor solution to a level where said organic compound is either positively or negatively ionized;
providing a hydrophilic acceptor solution;
adjusting the pH of said acceptor solution to a level wherein said compound, to be transferred from the donor solution to the acceptor solution, is ionized;
providing a liquid membrane comprising an immobilized organic solvent, which is substantially immiscible with water, through which a current and said at least one ionized organic compound can traverse;

and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution.

32. Process according to claim 31, wherein the voltage is in the range of 0.01V-30,000V.

33. Process according to claim 31, wherein DC voltage is applied.

34. Process according to claim 31, wherein a pulsed voltage is applied.

35. Process according to claim 31, wherein the donor solution is prepared from a biological sample.

36. Process according to claim 31, wherein the donor solution is prepared from an aqueous sample.

37. Process according to claim 31, wherein a donor solution is prepared by adjusting a pH of a donor solution to transfer an organic compound from a neutral state to a ionized ionic state.

38. Process according to claim 37, wherein a donor solution is prepared by transferring an organic compound to its anionic counterpart by adjusting the pH to a range from 8-14.

39. Process according to claim 37, wherein a donor solution is prepared by transferring an organic compound to its cationic counterpart by adjusting the pH to a range from 1-6.

40. Process according to claim 31, wherein an acceptor solution is prepared by adjusting the pH to a range from 8-14 in order to accept an anionic organic compound.

41. Process according to claim 31, wherein an acceptor solution is prepared by adjusting the pH to a range from 1-6 in order to accept a cationic organic compound.

42. Process according to claim 31, for increasing the concentration of at least one organic compound in said acceptor solution as compared to the concentration of said compound in the donor solution, wherein said increased concentration is achieved by providing a compartment for the acceptor solution, which is relatively smaller than the compartment of the donor solution.

43. Process according to claim 31, wherein the acceptor solution is used for quantitative and/or qualitative detection of the organic compound.

44. Process for concentration and/or enrichment of at least one organic compound, comprising the steps of providing a hydrophilic donor solution comprising at least one organic compound to be transferred from said donor solution to an acceptor solution;

adjusting the pH of said donor solution to a level where said organic compound is either positively or negatively ionized;

providing a hydrophilic acceptor solution;

adjusting the pH of said acceptor solution to a level wherein said compound, to be transferred from the donor solution to the acceptor solution, is ionized;

providing a liquid membrane comprising an immobilized organic solvent, which is substantially immiscible with water, through which a current and said at least one ionized organic compound can traverse;

and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution.

45. Process according to claim 44 wherein the donor solution is fed in a continuous or intermittent manner past said liquid membrane.

46. Process according to claim 44, wherein the acceptor solution is fed in a continuous or intermittent manner past the liquid membrane.

47. Process according to claim 44, wherein the process is conducted as a large-scale industrial process.

48. Process for preparing a sample for analysis, comprising the steps of providing a hydrophilic donor solution comprising at least one organic compound to be transferred from said donor solution to an acceptor solution;

adjusting the pH of said donor solution to a level where said organic compound is either positively or negatively ionized;

providing a hydrophilic acceptor solution;

adjusting the pH of said acceptor solution to a level wherein said compound, to be transferred from the donor solution to the acceptor solution, is ionized;

providing a liquid membrane comprising an immobilized organic solvent, which is substantially immiscible with water, through which a current and said at least one ionized organic compound can traverse;

and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution;

adjusting the pH of the acceptor solution to transfer said organic compound from an ionised to a non-ionized state and/or transferring the organic compound into an organic solvent, and detecting said organic compound by a suitable detector system and/or checking for biological activity in a biological test system.

49. Process according to claim 48, wherein the process is conducted in a system comprising a device incorporated in an analytical micro-chip device.

50. Process for purification of a sample, comprising the steps of providing a hydrophilic donor solution comprising at least one organic compound to be transferred from said donor solution to an acceptor solution;

adjusting the pH of said donor solution to a level where said organic compound is either positively or negatively ionized;

providing a hydrophilic acceptor solution;

adjusting the pH of said acceptor solution to a level wherein said compound, to be transferred from the donor solution to the acceptor solution, is ionized;

providing a liquid membrane comprising an immobilized organic solvent, which is substantially immiscible with water, through which a current and said at least one ionized organic compound can traverse;

and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution;

isolating said at least one organic compound through removal or replacement of the solvent.

51. Process for purification of a sample according to claim 50, wherein said at least one organic compound is detected, after optionally adjusting the pH of the acceptor solution and/or transferring the organic compound into an organic solvent, by a suitable detector system.

52. Process according to any of the claim 31, 44, 48 or 50, wherein said at least one organic compound after transferral to the acceptor solution is subjected to a test for biochemical activity.

53. Process according to any of the claim 31, 44, 48 or 50 wherein said at least one organic compound after transferral to the acceptor solution is subjected to one or more further reaction steps for chemical modification of said at least one organic compound.

54. Process according to any of the above claim 31, 44, 48 or 50 wherein said process comprises an additional step of agitating at least one of said donor or acceptor solutions.

* * * * *